(12) United States Patent
Chabrecek et al.

(10) Patent No.: US 6,835,410 B2
(45) Date of Patent: Dec. 28, 2004

(54) BOTTLE-BRUSH TYPE COATINGS WITH ENTANGLED HYDROPHILIC POLYMER

(75) Inventors: Peter Chabrecek, Riehen (CH); Jörg Leukel, Freiburg (DE); Dieter Lohmann, Münchenstein (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/142,300

(22) Filed: May 9, 2002

(65) Prior Publication Data

US 2003/0008063 A1 Jan. 9, 2003

(30) Foreign Application Priority Data

May 21, 2001 (EP) .............................................. 01810503

(51) Int. Cl.[7] .......................... A61L 27/00; B05D 1/02; B05D 1/18; B05D 1/36; B05D 1/38
(52) U.S. Cl. ...................... 427/2.24; 427/2.1; 427/2.31; 427/487; 427/508; 427/553; 427/558; 427/162; 427/164; 427/399; 427/301; 427/407.1; 427/414
(58) Field of Search ................................. 427/2.1, 2.24, 427/2.31, 487, 508, 553, 558, 162, 164, 299, 301, 407.1, 414

(56) References Cited

U.S. PATENT DOCUMENTS 6,387,379 B1 * 5/2002 Goldberg et al. ........... 424/400

FOREIGN PATENT DOCUMENTS

| EP | 1 095 966 A2 | | 5/2001 | |
| --- | --- | --- | --- | --- |
| EP | 1095966 | * | 5/2001 | .............. C08J/7/16 |
| WO | WO 96/20919 A | | 7/1996 | |
| WO | WO96 20919 | * | 7/1996 | ......... C07C/271/20 |
| WO | WO 99 57581 | * | 1/1999 | ............. G02B/1/04 |
| WO | WO 99/57581 A | | 11/1999 | |

OTHER PUBLICATIONS

International Search Report

* cited by examiner

*Primary Examiner*—Jennifer Kolb Michener
(74) *Attorney, Agent, or Firm*—Jian Zhou; Robert Gorman; R. Scott Meece

(57) ABSTRACT

The invention relates to a process for coating a material surface comprising the steps of:
  (a) providing an inorganic or organic bulk material having covalently bound to its surface initiator moieties for radical polymerization;
  (b) graft polymerizing a hydrophilic ethylenically unsaturated macromonomer from the bulk material surface in the presence of a biocompatible hydrophilic polymer being devoid of polymerizable ethylenically unsaturated groups and thereby entrapping said hydrophilic polymer within the polymer matrix formed by the polymerization of the macromonomer.

Composite materials obtainable according to the process of the invention have desirable characteristics regarding adherence to the substrate, durability, hydrophilicity, wettability, biocompatibility and permeability and are thus useful for the manufacture of biomedical articles such as ophthalmic devices.

17 Claims, No Drawings

BOTTLE-BRUSH TYPE COATINGS WITH ENTANGLED HYDROPHILIC POLYMER

This application claims under 35 U.S.C. §119(a)–(d) or §365(b) of European Patent Application No. 01810503.1 filed May 21, 2001.

The present invention relates to a process for coating articles, wherein the coating comprises a polymer having desirable characteristics regarding adherence to the substrate, durability, softness, hydrophilicity, lubricity, wettability, biocompatibility and permeability. More particular, the present invention relates to a process for coating an article, such as a biomedical material or article, especially a contact lens including an extended-wear contact lens, wherein the coating is composed of at least two individual hydrophilic polymer components. One of those hydrophilic components comprises polymer chains which are covalently bound to the substrate, whereas the second hydrophilic polymer is not covalently bound neither to the surface of the substrate nor to the polymer chains, but is being entrapped with said polymer chains.

Processes for preparing hydrophilic polymeric coatings on an "inert" hydrophobic substrate have been disclosed in the prior art. For example, WO 99/57581 discloses to first of all providing the article surface with covalently bound photoinitiator molecules, coating the modified surface with a layer of a polymerizable macromonomer and then subjecting it to a heat or radiation treatment whereby the macromonomer is graft polymerized thus forming the novel article surface. The covalent binding of the photoinitiator molecules to the article surface is created by first subjecting the article surface to a plasma treatment thereby providing the surface with functional groups, and then reacting said functional groups with co-reactive groups of a functional photoinitiator.

Surprisingly, it now has been found that articles, particularly biomedical devices such as contact lenses, with an even improved wettability, water-retention ability and biocompatibility are obtained by first of all providing the bulk material surface with covalently bound photoinitiator molecules, followed by grafting a hydrophilic ethylenically unsaturated macromonomer from the bulk material surface in the presence of a biocompatible hydrophilic polymer being devoid of polymerizable ethylenically unsaturated groups and thereby entrapping said biocompatible hydrophilic polymer within the polymer matrix formed by the polymerization of the macromonomer.

By this process, the macromonomer forms "bottle-brush" type tethered "hairy" chains on the bulk material surface having entangled a biocompatible hydrophilic polymer thereby forming a kind of semi-interpenetrating network (s-IPN) with the polymer chains of the macro-monomer.

The present invention therefore in one aspect relates to a process for coating a material surface comprising the steps of:

(a) providing an inorganic or organic bulk material having covalently bound to its surface initiator moieties for radical polymerization;

(b) graft polymerizing a hydrophilic ethylenically unsaturated macromonomer from the bulk material surface in the presence of a biocompatible hydrophilic polymer being devoid of polymerizable ethylenically unsaturated groups and thereby entrapping said hydrophilic polymer within the polymer matrix formed by the polymerization of the macromonomer.

Suitable bulk materials to be coated according to the invention are, for example, quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers or modified biopolymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. lotrafilcon A, neofocon, pasifocon, telefocon, silafocon, fluorsilfocon, paflufocon, elastofilcon, fluorofocon or teflon AF materials, such as teflon AF 1600 or teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred materials to be coated are amphiphilic segmented copolymers comprising at least one hydrophobic segment and at least one hydrophilic segment, which are linked through a bond or a bridge member. Examples are silicone hydrogels, for example those disclosed in PCT applications WO 96/31792 and WO 97/49740.

A particular preferred group of materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxafle, polytetrafluoroethylene, polyvinylchioride, DACRON® (a long-chain polyester made from ethylene glycol and tereophthalic acid), SILATIC® (a flexible inert silicone rubber), or a composite made therefrom.

The form of the material to be coated may vary within wide limits. Examples are particles, granules, capsules, fibres, tubes, films or membranes, preferably moldings of all kinds such as ophthalmic moldings, for example intraocular lenses, artificial cornea or in particular contact lenses.

The bonding of the photoinitiator moieties according to step (a) may be accomplished (i) according to the methods described in WO 99/57581, where the surface of the bulk material is first of all subjected to a plasma treatment thereby introducing reactive groups at the surface of the surface, followed by reaction of said reactive groups with an initiator moiety bearing co-reactive functional groups, or (ii) by reaction of certain hetero-bifunctional compounds at the surface of the bulk material said compounds having a first highly reactive functional group, which is able to react with the "inert" bulk material surface, and a second functional group for further covalent attachment of the initiator moieties.

Said hetero-bifunctional compound is, for example, a compound of formula

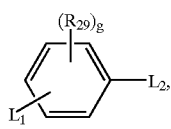

(1)

or $-N_3$ (2b)

wherein $R_{29}$ is $C_1$–$C_4$-alkyl, $C_1$–$C_4$-alkoxy, amino, hydroxy, sulfo, nitro, trifluoromethyl or halogen, g is an integer from 0 to 2, $L_1$ is a group, which functions as a triggerable precursor for carbene or nitrene formation, $L_2$ is amino, $C_1$–$C_4$-alkylamino, hydroxy, glycidyl, carboxy or a derivative thereof, isocyanato or isothiocyanato, or is a radical of formula

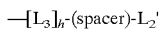

(1a), wherein $L_2'$ is amino, $C_1$–$C_4$-alkylamino, hydroxy, carboxy or a derivative thereof, isocyanato, isothiocyanato, —O-glycidyl or —O—C(O)—$(CH_2)_{h1}$—$X_2$, wherein h1 is from 1 to 4 and $X_2$ is carboxy or a derivative thereof, $L_3$ is —NH—, —N$C_1$–$C_6$-alkyl-, —O—, —C(O)O—, —C(O)NH—, —NHC(O)NH—, —NHC(O)O— or —OC(O)NH—;

(spacer) is linear or branched $C_1$–$C_{200}$-alkylene which may be substituted by hydroxy and/or interrupted by —O— except for $C_1$-alkyl, or is $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene; and h is the number 0 or 1.

$L_1$ in formula (1) is, for example, a group of formula

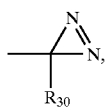

(2a)

wherein $R_{30}$ is an electron-withdrawing substituent, for example fluorinated $C_1$–$C_6$-alkyl, such as a radical —$C_2F_5$ or preferably a radical —$CF_3$.

$R_{29}$ is preferably $C_1$–$C_4$-alkoxy, nitro, $C_1$–$C_4$-alkyl, hydroxy, amino or sulfo. The variable g is, for example, 1 or preferably 0.

One group of suitable radicals of formula (1) are those wherein $L_1$ is a group

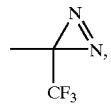

and g is 0. A further group of suitable radicals of formula (1) are those wherein $L_1$ is a group —$N_3$, and g is 1 or preferably 0.

Throughout the application the terms carboxy derivative, a derivative of carboxy and the like are to be understood as meaning, for example, a lactone, a carboxylic acid anhydride, halide, amide or ester, for example —C(O)Cl, —C(O)NH$_2$, —C(O)C$_1$–C$_6$-alkyl, —C(O)-phenyl or in particular an activated ester such as carboxy having been reacted with an activating agent, for example with N-hydroxy succinimide (NHS) or sulfo-N-hydroxy succinimide. A particularly preferred carboxy derivative is an activated ester of formula

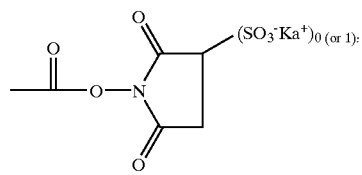

wherein $Ka^+$ is a cation, for example $Na^+$ or $K^+$.

The term glycidyl means a radical

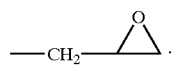

The bivalent radicals $L_3$ are always to be understood that the left bond is directed to the phenyl ring and the right bond is directed to the (spacer) radical.

According to one preferred embodiment of the invention, $L_2$ is amino, isocyanato, isothiocyanato, carboxy or a derivative thereof, and in particular amino, isocyanato, carboxy, or an activated carboxylic acid ester as mentioned above.

$L_3$ in formula (1a) is preferably a bivalent group —O—, —NH—, —C(O)O—, —C(O)NH— or —NHC(O)NH—, and is most preferably a radical —NH—, —C(O)O— or —C(O)NH—. h is preferably the number 1.

(spacer) in formula (1a) is preferably linear or branched, optional hydroxy-substituted, $C_1$–$C_{24}$-alkylene or $C_4$–$C_{160}$-alkylene which is interrupted by —O—, more preferably $C_1$–$C_{16}$-alkylene or $C_8$–$C_{160}$-alkylene which is interrupted by —O— and most preferably $C_2$–$C_{12}$-alkylene or —(alk')—O—$(CH_2CH_2O)_{18-160}$—(alk')—, wherein (alk') is, for example, $C_1$–$C_6$-alkylene, preferably $C_1$–$C_4$-alkylene more preferable $C_1$–$C_3$-alkylene and in particular 1,2-ethylene. If (spacer) is a cycloalkylene or mixed alkylene/cycloalkylene radical, the meanings and preferences given below for $R_{33}$ apply.

$L_2'$ is preferably amino, isocyanato, carboxy, a carboxy derivative, or a radical —O—C(O)—$(CH_2)_2$—$X_2$, wherein $X_2$ is carboxy or a derivative thereof. Particularly preferred meanings of $L_2'$ are amino, carboxy and an activated carboxylic acid ester as mentioned above.

A further preferred embodiment of the invention relates to the use of a compound of formula (1), wherein $L_2$ is a radical of formula (1a), $L_3$ is —NH—, —C(O)O— or—C(O)NH—, h is 1, (spacer) is linear $C_2$–$C_{12}$-alkylene or —($C_2$–$C_3$-alkylene)—O—$(CH_2CH_2O)_{18-160}$—($C_2$–$C_3$-alkylene)—, and $L_2'$ is carboxy, a carboxy derivative or a radical —O—C(O)—$(CH_2)_2$—$X_2$, wherein $X_2$ is carboxy or an activated carboxylic acid ester as mentioned above.

Preferably, $L_1$ is a group of formula

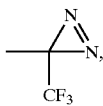

g is 0, and $L_2$ is carboxy, a carboxy derivative, or a radical of formula (1a) above, wherein the above-given meanings and preferences apply.

According to another preferred embodiment, $L_1$ is a group —$N_3$, g is 1 or preferably 0, $R_{29}$ is methyl, methoxy, hydroxy or nitro, and $L_2$ is amino, carboxy, a carboxy derivative, isocyanato, isothiocyanato or a radical of formula (1a) above, wherein the above-mentioned meanings and preferences apply, in particular amino.

The compounds of formula (1) may be applied to the material surface according to processes known per se. For example, the bulk material is immersed in a solution of a compound of formula (1), or a layer of a compound of formula (1) is first of all deposited on the bulk material surface to be modified, for example, by dipping, spraying, printing, spreading, pouring, rolling, spin coating or vacuum vapor deposition, with dipping or spraying being preferred. Most preferably, a solution comprising one or more different compounds of the formula (1) is sprayed onto the bulk material surface, which may be dry or preferably wet. The compound of formula (1) may be applied to the material surface in one cycle or in repeated cycles.

Suitable solvents useful as solvents of the compounds of formula (1) are, for example, water, $C_1$–$C_4$-alkanols such as methanol, ethanol or iso-propanol, nitrites such as acetonitrile, tetrahydrofuran (THF), aqueous solutions comprising an alkanol, THF or the like, ketones, for example acetone or methylethyl ketone, and also hydrocarbons, for example halogenated hydrocarbons such as methylene chloride or chloroform. The concentration of the compound of formula (1) in the spray solution depends on the specific compound used but is in general in the range of from 0.1 to 100 g/l, preferably 0.5 to 50 g/l, more preferably 0.5 to 25 g/l and in particular 1 to 10 g/l.

The fixation of the compounds of formula (1) on the bulk material surface then may be initiated, for example, by irradiation, particularly by irradiation with UV or visible light. Suitable light sources for the irradiation are known to the artisan and comprise for example mercury lamps, high pressure mercury lamps, xenon lamps, carbon arc lamps or sunlight. Sensitizers may be used to shift the irradiation wavelength. In addition, a suitable filter may be used to limit the irradiation to a specific wavelength range. Preferably, the bulk material surface to which the compound(s) of formula (1) have been previously applied, is irradiated with light of a wavelength $\geq$250 nm and preferably $\geq$300 nm. The time period of irradiation is not critical but is usually in the range of up to 30 minutes, preferably from 10 seconds to 10 minutes, and more preferably from 15 seconds to 5 minutes, and particularly preferably from 20 seconds to 1 minute. The irradiation may be carried out under ambient conditions or in an atmosphere of inert gas. Masks can be used for the generation of specific surface patterns of functional groups. Following the fixation reaction, any non-covalently bound compounds can be removed, for example by treatment, e.g. extraction, with suitable solvents, for example water, $C_1$–$C_4$-alkanols, water/$C_1$–$C_4$-alkanol mixtures or acetonitrile.

Depending on the desired concentration of functional groups $L_2$ on the material surface, the above outlined process cycle, (i) contacting, i.e. spraying or dipping, the surface with the compound(s) of formula (1) and (ii) fixing the compound(s) of formula (1) on the surface, i.e. by irradiation, may be carried out once or, preferably, several times. For example, 1 to 100, preferably 1 to 50 and in particular 5 to 25, different layers of one or more compounds of formula (1) are added and fixed on the material surface.

A polymerization initiator according to step (a) is typically one that is initiating a radical polymerization of ethylenically unsaturated compounds. The radical polymerization may be induced thermally, or preferably by irradiation.

Initiators for the thermal polymerization are particularly functional initiators having an initiator part such as a peroxide, hydroperoxide, persulfate or azo group and in addition a functional group that is co-reactive with the functional groups $L_2$ of the modified bulk material surface obtainable, for example, as described above or as disclosed in WO 99/57581. Suitable functional groups that are co-reactive with $L_2$ are, for example, a carboxy, amino, hydroxy, epoxy or isocyanato group.

Initiators for the radiation-induced polymerization are particularly functional photoinitiators having a photoinitiator part and in addition a functional group that is co-reactive with the functional groups introduced to the bulk material surface by a plasma treatment according to step (i), or that is co-reactive with the functional groups $L_2$ of the bulk material surface modified according step (ii). The photoinitiator part may belong to different types, for example to the thioxanthone type and preferably to the benzoin type. Suitable functional groups that are co-reactive with $L_2$ are, for example, a carboxy, amino, hydroxy, epoxy or isocyanato group.

Preferred polymerization initiators for use in the present invention are the photoinitiators of formulae (l) and (la) as disclosed in U.S. Pat. No. 5,527,925, those of the formula (I) as disclosed in PCT application WO 96/20919, or those of formulae II and III including formulae IIa–IIy and IIIg as disclosed in EP-A-0281941, particularly formulae IIb, IIi, IIm, IIn, IIp, IIr, IIs, IIx and IIIg therein.

The polymerization initiator moieties are preferably derived from a functional photoinitiator of the formula

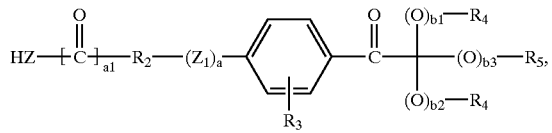

(3a)

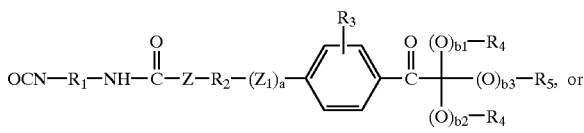

(3b)

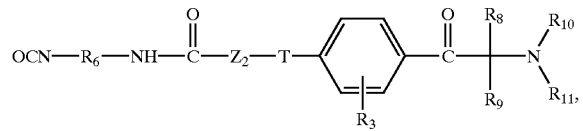

(3c)

wherein b1 and b2 are each 0, Z and $Z_1$ are each bivalent —O—, b3 is 0 or 1; $R_4$ is methyl or phenyl, or both groups $R_4$ together are pentamethylene; $R_5$ is methyl or H; $R_3$ is hydrogen; a is 1 and $R_2$ is ethylene, or a is 0 and $R_2$ is a direct bond; a1 is 0 or 1; and $R_1$ is branched $C_6$–$C_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-$CH_2$— or cyclohexyl-$CH_2$— substituted by from 1 to 3 methyl groups, T is bivalent —O—; $Z_2$ is —O—$(CH_2)_y$— wherein y is an integer from 1 to 4 and the terminal $CH_2$ group of which is linked to the adjacent T in formula (3c); $R_3$ is H; $R_8$ is methyl, allyl, tolylmethyl or benzyl, $R_9$ is methyl, ethyl, benzyl or phenyl, or $R_8$ and $R_9$ together are pentamethylene, $R_{10}$ and $R_{11}$ are each independently of the other $C_1$–$C_4$-alkyl or $R_{10}$ and $R_{11}$ together are —$CH_2CH_2OCH_2CH_2$—, and $R_6$ is branched $C_6$–$C_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-$CH_2$— or cyclohexylene-$CH_2$— substituted by from 1 to 3 methyl groups.

Photoinitiators of formula (3a) and (3b) are particularly preferred.

Some examples of especially preferred functional photoinitiators are the compounds of formulae

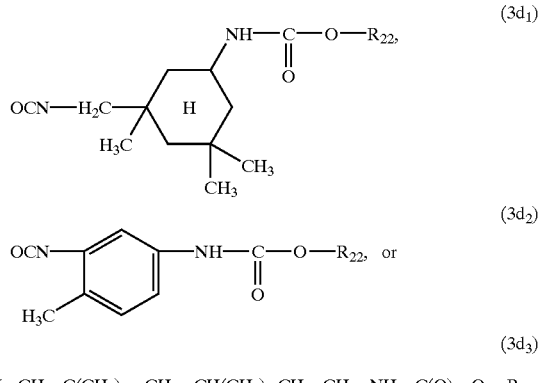

wherein $R_{22}$ is a radical

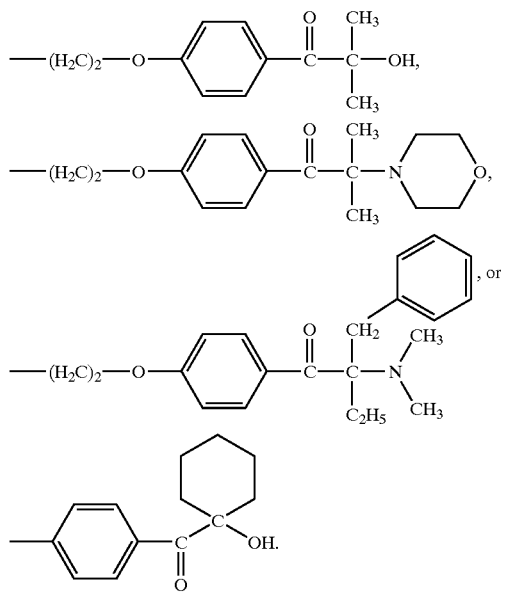

The reactions of radicals on the material surface that are derived from a compound of formula (1) having a carboxy, carboxy derivative, isocyanato or isothiocyanato group $L_2$ with a functional polymerisation initiator having an amino or hydroxy group, or vice versa, are well-known in the art and may be carried out as desribed in textbooks of organic chemistry. For example, the reaction of a radical derived from a compound of formula (1), wherein $L_2$ is an isocyanato or isothiocyanato group with an amino- or hydroxy- functionalized polymerisation initiator, or vice versa the reaction of an amino- or hydroxy group $L_2$ with an isocyanato or isothiocyanato functionalized polymerisation initiator, may be carried out in an inert organic solvent such as an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. It is advantageous to carry out the above reactions under an inert atmosphere, for example under a nitrogen or argon atmosphere.

In case that the radicals on the material surface are derived from a compound of formula (1) having a carboxy group $L_2$, the reaction of the carboxy group with an amino or hydroxy group functionalized photoinitiator, or vice versa the reaction of an amino or hydroxy group $L_2$ with a carboxy functionalized polymerisation initiator, may be carried out under the conditions that are customary for ester or amide formation, for example in an aprotic medium at a temperature from about room temperature to about 100° C. It is further preferred to carry out the esterification or amidation reaction in the presence of an activating agent, for example N-ethyl-N'-(3-dimethylaminopropyl)carbodiimide (EDC), N-hydroxy succinimide (NHS), sulfo-N-hydroxy succinimide or N,N'-dicyclohexyl carbodiimide (DCC) or in the presence of an o-(benztriazole)-uronium salt such as o-(benztriazol-1-y-)-N,N,N,N-tetramethyluronium hexafluorophosphate. Most preferably, the carboxy group $L_2$ is previously converted to an activated ester using one of the above-mentioned activating agents, and the activated ester is then further reacted with the hydroxy or preferably amino groups of the surface.

In a preferred embodiment of the invention, $L_2$ comprises amino, alkylamino or hydroxy, particularly amino, as reactive group and the co-reactive group of the polymerization initiator is an isocyanato group. A preferred polymerization initiator of this embodiment is a photoinitiator of the above formula (3b), (3c), ($3d_1$), ($3d_2$) or ($3d_3$).

According to another preferred embodiment of the invention, $L_2$ comprises carboxy, a carboxy derivative, isocyanato or isothiocyanato as reactive group, and the co-reactive group of the polymerization initiator is a hydroxy, amino, alkylamino or thiol group, particularly an amino group. A preferred polymerization initiator of this embodiment is a photoinitiator of the above formula (3a).

Hydrophilic ethylenically unsaturated macromonomers for graft polymerization from the bulk material surface according to step (b) of the process of the present invention are known, for example, from WO 99/57581. A suitable macromonomer is, for example of formula

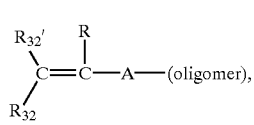

wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

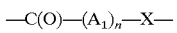         (5a) or

—(A$_2$)$_m$—NH—C(O)—X— (5b) or

—(A$_2$)$_m$—X—C(O)— (5c) or

—C(O)—NH—C(O)—X— (5d) or

—C(O)—X$_1$—(alk*)—X—C(O)— (5e) or

A and R$_{32}$, together with the adjacent double bond, are a radical of formula

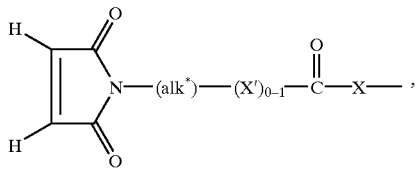

(5f)

A$_1$ is —O—C$_2$–C$_{12}$-alkylene which is unsubstituted or substituted by hydroxy, or is —O—C$_2$–C$_{12}$-alkylene-NH—C(O)— or —O—C$_2$–C$_{12}$-alkylene-O—C(O)—NH—R$_{33}$—NH—C(O)— or —NH—(Alk*)—C(O)—, wherein (Alk*) is C$_1$–C$_6$-alkylene and R$_{33}$ is linear or branched C$_1$—C$_{18}$-alkylene or unsubstituted or C$_1$–C$_4$-alkyl- or C$_1$–C$_4$-alkoxy-substituted C$_6$—C$_{10}$-arylene, C$_7$–C$_{18}$-aralkylene, C$_6$–C$_{10}$-arylene-C$_1$–C$_2$-alkylene-C$_6$–C$_{10}$-arylene, C$_3$–C$_8$-cycloalklene, C$_3$–C$_8$-cycloalklene-C$_1$–C$_6$-alkylene C$_3$–C$_8$-cycloalkylene-C$_1$–C$_2$-alkylene-C$_3$–C$_8$-cycloalklene or C$_1$–C$_6$-alkylene-C$_3$–C$_8$-cycloalkylene-C$_1$–C$_6$-alkylene;

A$_2$ is C$_1$–C$_8$-alkylene; phenylene or benzylene;

m and n are each independently of the other the number 0 or 1;

X, X$_1$ and X' are each independently of the other a bivalent group —O— or —NR", wherein R" is hydrogen or C$_1$–C$_6$-alkyl;

(alk*) is C$_2$–C$_{12}$-alkylene;

and (oligomer) denotes (i) the radical of a telomer of formula

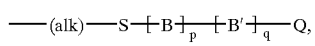

(6a)

wherein (alk) is C$_2$–C$_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

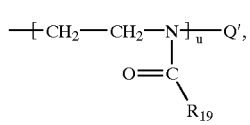

(6b)

wherein R$_{19}$ is hydrogen or unsubstituted or hydroxy-substituted C$_1$–C$_{12}$-alkyl, u is an integer from 2 to 250 and Q' is a radical of a polymerization initiator; or (iii) the radical of formula

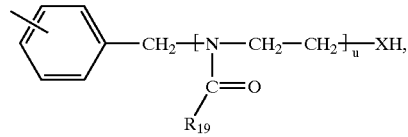

(6b')

wherein R$_{19}$, X and u are as defined above, or (iv) the radical of an oligomer of formula

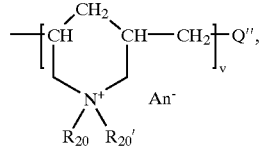

(6c)

wherein R$_{20}$ and R$_{20}$' are each independently C$_1$–C$_4$-alkyl, An$^-$ is an anion, v is an integer from 2 to 250, and Q" is a monovalent group that is suitable to act as a polymerization chain-reaction terminator; or (v) the radical of an oligopeptide of formula —(CHR$_{21}$—C(O)—NH)$_t$—CHR$_{21}$—COOH (6d) or —CHR$_{21}$—(NH—C(O)—CHR$_{21}$)$_t$—NH$_2$ (6d'), wherein R$_{21}$ is hydrogen or C$_1$–C$_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula —(alk**—O)$_z$—[CH$_2$—CH$_2$—O]$_r$—[CH$_2$—CH(CH$_3$)—O]$_s$
—R$_{34}$ (6e), wherein R$_{34}$ is hydrogen or C$_1$–C$_{24}$-alkyl, (alk**) is C$_2$–C$_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (5a), (5b) or (5d) or A and R$_{32}$, together with the adjacent double bond, are a radical of formula (5f) if (oligomer) is a radical of formula (6b), (6c), (6d) or (6e) or is the radical of an oligosaccharide;

A is a direct bond if (oligomer) is a radical of formula (6b'); and

A is a radical of formula (5c) or (5e) if (oligomer) is a radical of formula (6d').

The following preferences apply to the variables contained in the definition of the macromonomer of formula (4):

R' is preferably hydrogen or C$_1$–C$_4$-alkyl, more preferably hydrogen or C$_1$–C$_2$-alkyl and particularly preferably hydrogen.

R$_{32}$ is preferably hydrogen, methyl or carboxyl, and particularly preferably hydrogen.

R is preferably hydrogen or methyl.

X is preferably a bivalent group —O— or —NH—. X is particularly preferably the group —NH— if (oligomer) is a radical of formula (6a); (6c) or (6d), and is particularly preferably the group —O— if (oligomer) is a radical of formula (6b) or (6e) or is the radical of an oligosaccharide. X' is preferably —O— or —NH— and more preferably —NH—. $X_1$ is preferably —O— or —NH—.

The radical $R_{33}$ has a symmetrical or, preferably, an asymmetrical structure. $R_{33}$ is preferably linear or branched $C_6$–$C_{10}$alkylene; cyclohexylene-methylene or cyclohexylene-methylene cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{33}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl iso-cyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene-NH—C(O)— and particularly —O—(CH$_2$)$_{2-4}$—, —O—CH$_2$—CH(OH)—CH$_2$— or a radical —O—(CH$_2$)$_{2-4}$—NH—C(O)—. A particularly preferred meaning of $A_1$ is the radical —O—(CH$_2$)$_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene. n is an integer of 0 or preferably 1. m is preferably an integer of 1 $R_{32}$' is preferably hydrogen or methyl and particularly preferably hydrogen. In case that (oligomer) is a radical of formula (6a), (6b), (6c), (6d) or (6e) or is the radical of an oligosaccharide, is A preferably a radical of formula (5a) or (5b) and particularly preferably a radical of formula (5a), wherein the above given meanings and preferences apply for the variables contained therein.

A preferred group of hydrophilic macromonomers according to the invention comprises compounds of the above formula (4), wherein R is hydrogen or methyl, $R_{32}$ is hydrogen, methyl or carboxyl, $R_{32}$' is hydrogen, A is a radical of the formula (5a) or (5b) and (oligomer) is a radical of formula (6a), (6b), (6c), (6d) or (6e) or is the radical of an oligosaccharide. An even more preferred group of hydrophilic macromonomers comprises compounds of the above formula (4), wherein R is hydrogen or methyl, $R_{32}$ and $R_{32}$' are each hydrogen, A is a radical of the formula (5a) and (oligomer) is a radical of formula (6a). A further group of preferred macromonomers comprises compounds of formula (4), wherein A is a radical of formula (5e) above and (oligomer) is a radical of formula (6a).

(Alk*) is preferably methylene, ethylene or 1,1-dimethyl-methylene, in particular a radical —CH$_2$— or —C(CH$_3$)$_2$—. (alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50.

Suitable hydrophilic substituents of the radicals B or B' are those described in WO 99/57581 on pages 16 to 24.

A group of preferred non-ionic substituents of B or B' comprises $C_1$–$C_2$-alkyl, which is unsubstituted or substituted by —OH or —NR$_{23}$R$_{23}$', wherein R$_{23}$ and R$_{23}$' are each independently of the other hydrogen or $C_1$–$C_2$-alkyl; a radical —COOY wherein Y is $C_1$–$C_4$-alkyl; $C_2$–$C_4$-alkyl which is substituted by —OH, —NR$_{23}$R$_{23}$' wherein R$_{23}$ and R$_{23}$' are each independently of another hydrogen or $C_1$–$C_2$-alkyl, or Y is a radical —$C_2$–$C_4$-alkylene-NH—C(O)—O—G wherein —O—G is the radical of a saccharide; a radical —C(O)—NY$_1$Y$_2$, wherein Y$_1$ and Y$_2$ are each independently of the other hydrogen or $C_1$–$C_6$-alkyl which is unsubstituted or substituted by hydroxy, or Y$_1$ and Y$_2$ together with the adjacent N-atom form a heterocyclic 6-membered ring having no further heteroatom or having one further N- or O-atom; a radical —OY$_3$, wherein Y$_3$ is hydrogen, $C_1$–$C_4$-alkyl which is unsubstituted or substituted by —NH$_2$ or —N($C_1$–$C_2$-alkyl)$_2$, or is a group —C(O)$C_1$–$C_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose; a radical —CO—NY$_1$Y$_2$, wherein Y$_1$ and Y$_2$ are each independently of the other hydrogen or $C_1$–$C_4$-alkyl which is unsubstituted or substituted by hydroxy, or Y$_1$ and Y$_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —CONH$_2$, —CON(CH$_3$)$_2$,

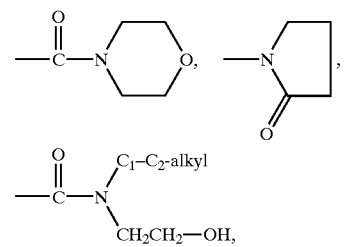

—CONH—(CH$_2$)$_2$—OH, —COO—(CH$_2$)$_2$—N(CH$_3$)$_2$, and —COO(CH$_2$)$_{2-4}$—NHC(O)—O—G wherein —O—G is the radical of trehalose.

Particularly preferred anionic substituents of B or B' are —COOH, —SO$_3$H, o-, m- or p-sulfophenyl, o-, m- or p-sulfomethylphenyl or a radical —CONY$_5$Y$_6$, wherein Y$_5$ is $C_2$–$C_4$-alkyl substituted by sulfo, and Y$_6$ is hydrogen.

A preferred cationic substituent of B or B' is a radical —C(O)OY$_7$ wherein Y$_7$ is $C_2$–$C_4$-alkyl, which is substituted by —N($C_1$–$C_2$-alkyl)$_3$$^+$An$^-$ and is further substituted by hydroxy, and An$^-$ is an anion, for example the radical —C(O)O—CH$_2$—CH(OH)—CH$_2$—N(CH$_3$)$_3$$^+$An$^-$.

A preferred group of zwitter-ionic substituents —R$_{24}$—Zw corresponds to the formula

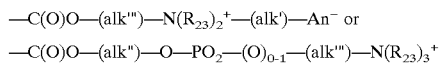

wherein R$_{23}$ is hydrogen or $C_1$–$C_6$-alkyl; An$^+$ is an anionic group —COO$^-$, —SO$_3$$^-$ or —OPO$_3$H$^-$, preferably —COO$^-$ or —SO$_3^-$ and most preferably —SO$_3^-$, alk' is C$_1$–C$_{12}$-alkylene, (alk") is C$_2$–C$_{24}$-alkylene which is unsubstituted or substituted by a radical —OY$_8$, Y$_8$ is hydrogen or the acyl radical of a carboxylic acid, and (alk''') is C$_2$–C$_8$-alkylene.

(alk') is preferably C$_2$–C$_8$-alkylene, more preferably C$_2$–C$_6$-alkylene and most preferably C$_2$–C$_4$-alkylene. (alk") is preferably C$_2$–C$_{12}$-alkylene, more preferably C$_2$–C$_6$-alkylene and particularly preferably C$_2$–C$_3$-alkylene which is in each case unsubstituted or substituted by hydroxy or by a radical —OY$_8$. (alk''') is preferably C$_2$–C$_4$-alkylene and more preferably C$_2$–C$_3$-alkylene R$_{23}$ is hydrogen or C$_1$–C$_4$-alkyl, more preferably methyl or ethyl and particularly preferably methyl. A preferred zwitterionic substituent of B or B' is of formula

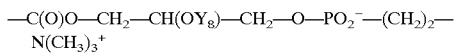

wherein Y$_8$ is hydrogen or the acyl radical of a higher fatty acid.

B denotes for example a radical of formula

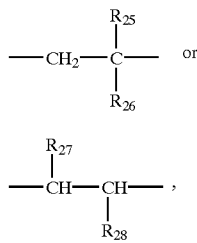

wherein R$_{25}$ is hydrogen or C$_1$–C$_4$-alkyl, preferably hydrogen or methyl; R$_{26}$ is a hydrophilic substituent, wherein the above given meanings and preferences apply; R$_{27}$ is C$_1$–C$_4$-alkyl, phenyl or a radical —C(O)OY$_9$, wherein Y$_9$ is hydrogen or unsubstituted or hydroxy-substituted C$_1$–C$_4$-alkyl; and R$_{28}$ is a radical —C(O)Y$_9$' or —CH$_2$—C(O)OY$_9$' wherein Y$_9$' independently has the meaning of Y$_9$.

R$_{27}$ is preferably C$_1$–C$_2$-alkyl, phenyl or a group —C(O)OY$_9$. R$_{28}$ is preferably a group —C(O)OY$_9$' or —CH$_2$—C(O)OY$_9$' wherein Y$_9$ and Y$_9$' are each independently of the other hydrogen, C$_1$–C$_2$-alkyl or hydroxy-C$_1$–C$_2$-alkyl. Particularly preferred —CHR$_{27}$—CHR$_{28}$— units according to the invention are those wherein R$_{27}$ is methyl or a group —C(O)OY$_9$ and R$_{28}$ is a group —C(O)OY$_9$' or —CH$_2$—C(O)OY$_9$' wherein Y$_9$ and Y$_9$' are each hydrogen, C$_1$–C$_2$-alkyl or hydroxy-C$_1$–C$_2$-alkyl.

B' independently may have one of the meanings given above for B.

If (oligomer) is a radical of formula (6a), the radical —(alk)—S—[B]$_p$—[B']$_q$—Q preferably denotes a radical of formula

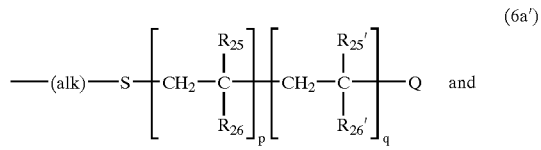

even more preferably of the formula

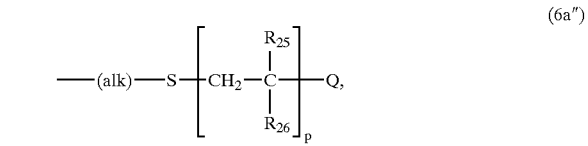

wherein for R$_{25}$, R$_{26}$, Q, p and q the above-given meanings and preferences apply, for R$_{25}$' independently the meanings and preferences given before for R$_{25}$ apply, and for R$_{26}$' independently the meanings and preferences given before for R$_{26}$ apply.

A preferred group of suitable hydrophilic macromonomers according to step (b) of the invention comprises compounds of formula

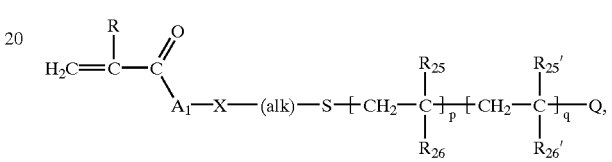

wherein R is hydrogen or methyl, A$_1$ is —O—(CH$_2$)$_{2-4}$—, —O—CH$_2$—CH(OH)—CH$_2$— or a radical —O—(CH$_2$)$_{2-4}$—NH—C(O)—, X is —O— or —NH—, (alk) is C$_2$–C$_4$-alkylene, Q is a monovalent group that is suitable to act as a polymerization chain-reaction terminator, p is an integer from 5 to 50, R$_{25}$ and R$_{25}$' are each independently of the other hydrogen or methyl, and for R$_{26}$ and R$_{26}$' each independently the above given meanings and preferences apply.

A particularly preferred embodiment of the invention relates to hydrophilic macromonomers of the formula

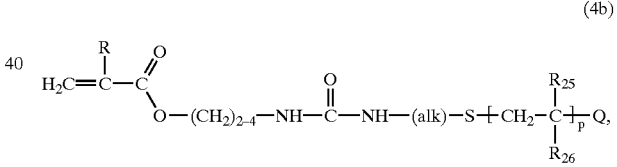

wherein for R, R$_{25}$, R$_{26}$, Q, (alk) and p the above-given meanings and preferences apply. A particularly preferred group of hydrophilic macromonomers are compounds of the above formula (4b) wherein R is hydrogen or methyl, (alk) is C$_2$–C$_4$-alkylene, R$_{25}$ is hydrogen or methyl, p is an integer of 5 to 50, Q is as defined before, and for R$_{26}$ the above given meanings and preferences apply; in particular R$_{26}$ of this embodiment is a radical —CONH$_2$, —CON(CH$_3$)$_2$ or

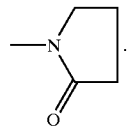

If (oligomer) is a radical (ii) of formula (6b), Q' in formula (6b) is for example C$_1$–C$_{12}$-alkyl, phenyl or benzyl, preferably C$_1$–C$_2$-alkyl or benzyl and in particular methyl. R$_{19}$ is preferably unsubstituted or hydroxy-substituted C$_1$–C$_4$-alkyl and in particular methyl. u is preferably an integer from 2 to 150, more preferably from 5 to 100, even more preferably from 5 to 75 and particularly preferably from 10 to 50.

If (oligomer) is a radical of formula (6b'), the above given meanings and preferences apply for the variables $R_{19}$ and u contained therein. X in formula (6b') is preferably hydroxy or amino.

If (oligomer) denotes a radical (iv) of formula (6c), $R_{20}$ and $R_{20}'$ are each preferably ethyl or in particular methyl; v is preferably an integer from 2 to 150, more preferably from 5 to 100, even more preferably from 5 to 75 and particularly preferably from 10 to 50; Q" is for example hydrogen; and An⁻ is as defined before.

If (oligomer) denotes an oligopeptide radical (v) of formula (6d) or 6d'), $R_{21}$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —(CH₂)₃—NH—C(=NH)—NH₂. t is preferably an integer from 2 to 150, more preferably from 5 to 100, even more preferably from 5 to 75 and particularly preferably from 10 to 50.

If (oligomer) denotes a polyoxyalkylene radical (vi) of formula (6e), $R_{34}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl. (alk **) is preferably a $C_2$–$C_3$-alkylene radical. z is preferably 0. r and s are each independently preferably an integer from 0 to 100 wherein the total of (r+s) is 5 to 100. r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0. (oligomer) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25,000 Da, preferably up to 10,000 Da. Preferably the oligosaccharide according to (vii) is the radical of a cyclodextrin with a maximum of 8 sugar units.

Formulae (6a), (6a') or (6e) are to be understood as a statistic description of the respective oligomeric radicals, that is to say, the orientation of the monomers and the sequence of the monomers (in case of copolymers) are not fixed in any way by said formulae. The arrangement of B and B' in formula (6a) or of the ethyleneoxide and propyleneoxide units in formula (6e) thus in each case may be random or blockwise.

The weight average molecular weight of the hydrophilic macromonomer according to step (b) depends principally on the desired properties and is for example from 300 to 25000 Da, preferably from 300 to 12,000 Da, more preferably from 300 to 8000 Da, even more preferably from 300 to 5000 Da, and particularly preferably from 500 to 4000 Da.

The macromonomers of formula (4) may be prepared by methods known per se, as described in, for example, WO 99/57581.

A wide variety of structurally different polymers are suitable for use in step (b) of the present invention subject to the condition that said polymers lack polymerizable ethylenically unsaturated groups and are hydrophilic and biocompatible. Suitable biocompatible hydrophilic polymers comprise, for example, biopolymers, modified biopolymers and synthetic polymers.

The weight average molecular weight $M_w$ of biocompatible hydrophilic polymers according to step (b) depends principally on the desired properties and is from 1000 to 5,000,000 Da, preferably from 10,000 to 1,000,000 Da, and particularly preferably from 100,000 to 500,000 Da.

Examples of suitable biopolymers are polysaccharides, for example, hyaluronic acid, chondriotin sulfate, dextran, 1,3-glucan, fucoidan; glycoproteins, for example, mucin, fibronectin; glucosamines, for example chitin, chitosan, heparin; polypeptides, for example, lysozyme, collagen; proteins, for example albumen, immunoglobulines.

Examples of suitable modified biopolymers are, for example, carboxyalkylcellulose, for example carboxymethylcellulose, carboxyalkylchitin, carboxyalkylchitosan.

Examples of suitable synthetic polymers are bis-aminoalkylene-polyalkylefle glycols of various average molecular weights, for example JEFFAMINE® polyoxyalkylene amines; polyethyleneglycols, poly(hydroxyethyl methacrylate (poly-HEMA), high molecular weight, crosslinked, acrylic acid based polymers, for example, Carbopol® polymers (high molecular weight homo- and copolymers of acrylic acid crosslinked with a polyalkenyl polyether) and NOVEON® Polycarbophils (polymers of acrylic acid crosslinked with divinyl alcohol. polyacrylamide, polyvinylpyrrolidone, polyvinyl alcohol.

Preferred biocompatible hydrophilic polymers are highly branched and/or possess molecular weights >40,000 Da. Especially preferred are hyarulonic acid, dextran, heparin, chondriotin sulfate, mucin, polyvinylpyrrolidone or a NOVEON® Polycarbophil or Carbopol® polymer.

The biocompatible hydrophilic polymer is not covalently bonded to the polymer chains of the macromonomer. Chain entanglement, hydrogen bonds, Van der Waals forces and charge interactions are among the most important interactions between the hydrophilic macromonomers grafted from the bulk material and the biocompatible hydrophilic polymer. These forces stabilize the entangled biocompatible hydrophilic polymer and prevent it's rapid leaching from the interpenetration mixture under physiological conditions. Preferably, the biocompatible hydrophilic polymers contribute significantly to specific advantageous features of the s-IPN-structured coating. Among those are for example: lubrication, water retention and stabilization of aqueous surface layers, biocompatibility, reversible attraction of biomolecules (e.g. mucins) from biological fluids, prevention of irreversible deposition of proteins, lipids and salts and inhibition of microbial adhesion. Controlled low rate leaching of entangled biocompatible hydrophilic polymers out of the contact lens coatings can enhance lubricity and comfort, and in addition can favour a continuous renewal of the lens surface.

Additional components can be included within the s-IPN. They can either be uncrosslinked polymers, oligomers or low molecular weight components with their leaching rates from the s-IPN naturally increasing with descreasing molecular masses. An additional component is preferably a bioactive material or a bioactive polymer. In a particular embodiment of the invention an additional component can be an enzyme, an antibody, an antimicrobial peptide, a polyquat or a growth factor. It is characteristic for additional components that they slowly release from the coating under physiological conditions.

The practical use of devices and articles carrying coatings according to the disclosed technology can be seen in technical, in biological and in environmental systems. Applications in the biomedical field are preferred: in particular, coatings for ophthalmic devices and implants, such as contact lenses, ocular drug delivery systems, intraocular lenses and artificial corneas.

In addition, s-IPN coatings of the present invention are outstanding with regard to their capability of lubricating contact lens surfaces and thus reducing the blinking frequency and the overall wearing comfort of contact lens users. By lubricating the cornea surface (via leachables) contact lens coatings of the present invention can improve the on-eye mobility of contact lens. All this is of particular importance with regard to extended wear contact lenses. These advantageous effects can be caused or be enhanced by leaching of B and/or C. The surface coatings of the invention can also be applied to ophthalmic implants. In technical applications coatings of the present invention can prevent befouling of separation membranes and can reduce friction, calcification, scale and drag phenomena in hydrodynamic systems.

The mixture of hydrophilic macromonomers and biocompatible hydrophilic polymer may be applied to the initiator-modified material according to processes known per se. For example, the material comprising the covalently bound polymerisation initiator is immersed in a solution of the macromonomer and biocompatible hydrophilic polymer, or a layer of said solution is first of all deposited on the modified material surface, for example, by dipping, spraying, spreading, knife coating, pouring, rolling, spin coating or vacuum vapor deposition. Suitable solvents, if used in the polymerization process, are, for example, water or dipolar aprotic solvents such as, for example, acetonitrile. The polymerization of the hydrophilic macromonomer on the material surface then may be initiated , for example, thermally by the action of heat or preferably by irradiation, particularly by UV radiation. Suitable light sources for the irradiation are known to the artisan and comprise for example mercury lamps, high-pressure mercury lamps, xenon lamps, carbon arc lamps or sunlight. The time period of irradiation may depend for example on the desired properties of the resulting composite material but is usually in the range of up to 30 minutes, preferably from 10 seconds to 10 minutes, and particularly preferably from 0.5 to 5 minutes. It is advantageous to carry out the irradiation in an atmosphere of inert gas.

The coated material obtained according to the invention may be purified afterwards in a manner known per se, for example by washing or extraction with a suitable solvent such as water.

By means of process step (b) of the above-described coating process, the hydrophilic macromonomers may be grafted to the material surface with formation of a coating having, for example, a so-called bottle brush-type structure (BBT) composed of tethered "hairy" chains. Such BBT structures in one embodiment comprise a long hydrophilic or hydrophobic backbone, which carries relatively densely, packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

A further embodiment of the invention relates to a material that is coated by the process of the invention.

The material that is coated by the process of the invention is, for example, an organic bulk material, preferably a biomedical device, e.g. an ophthalmic device, preferably a contact lens including both hard and particularly soft contact lenses, an intraocular lens or artificial cornea. Further examples are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices, e.g. ophthalmic devices obtained according to the invention have a variety of unexpected advantages over those of the prior art which make those devices very suitable for practical purposes, e.g. as contact lens for extended wear or intraocular lens. For example, they do have a high surface wettability, which can be demonstrated by their contact angles, their water retention and their water-film break up time or tear film break up time (TBUT).

The TBUT plays a particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer that lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, those made of nelfilcon A, vifilcon A or lotrafilcon A polymer, by applying a surface coating according to the invention. On the base curve of a contact lens, the pronounced lubricity of the coating facilitates the on-eye lens movement, which is essential for extended wear of contact lenses. Moreover, the materials obtained by the process of the invention provide additional effects being essential for lenses for extended wear, such as an increased thickness of the pre-lens tear film which contributes substantially to low microbial adhesion and resistance to deposit formation. Due to the very slow release of the biocompatible hydrophilic polymer the surface coatings according to the present invention are extremely soft and lubricious. Biomedical articles such as in particular contact lenses coated by the process of the invention show a superior wearing comfort including improvements with respect to late day dryness and long term (overnight) wear. The novel surface coatings moreover interact in a reversible manner with ocular mucus, which contributes to the improved wearing comfort.

In addition, biomedical devices, e.g. ophthalmic devices such as contact lenses, coated by the process of the invention, have a very pronounced biocompatibility combined with good mechanical properties. For example, the devices are blood compatible and have good tissue integration. In addition, there are generally no adverse eye effects observed, while the adsorption of proteins or lipids are low, also the salt deposit formation is lower than with conventional contact lenses. Generally, there is low fouling, low microbial adhesion and low bio erosion while good mechanical properties can be for example found in a low friction coefficient and low abrasion properties. Moreover, the dimensional stability of the materials obtained according to the invention is excellent. In addition, the attachment of a hydrophilic surface coating at a given bulk material according to the invention does not affect its visual transparency.

In summary, the ophthalmic devices obtained by the process of the invention, such as contact lenses and artificial cornea, provide a combination of low spoilation with respect to cell debris, cosmetics, dust or dirt, solvent vapors or chemicals, with a high comfort for the patient wearing such ophthalmic devices in view of the soft hydrogel surface which for example provides a very good on-eye movement of the ophthalmic device.

Biomedical devices such as renal dialysis membranes, blood storage bags, pacemaker leads or vascular grafts coated by the process of the invention resist fouling by proteins by virtue of the continuous layer of bound water, thus reducing the rate and extent of thrombosis. Blood-contacting devices fabricated according to the present invention are therefore haemocompatible and biocompatible.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Krüss GmbH, Hamburg, Germany). Wetting force on the solid is measured as the solid is immersed in or withdrawn from a liquid of known surface tension.

EXAMPLE A-1
1,2-Diaminocyclohexane Plasma Coating (DACH)

Two dried Lotrafilcon A lenses (polysiloxane/perfluoroether copolymer) are, after extraction in isopropanol, toluene and again in isopropanol, placed on the glass holder within the plasma reactor equipped with an external ring electrode and a 27.13 MHz radiofrequency (RF) generator for the generation of an inductively-coupled, cold glow discharge plasma. The distance between the substrates and the lower edge of the plasma zone is 12 cm. The reactor is evacuated to a pressure of 0.008 mbar, and held at these conditions for 1 h. Then, the argon plasma gas flow rate into the plasma zone of the reactor is set to 20 sccm (standard cubic centimeter), the pressure in the reactor is adjusted to 0.12 mbar and the RF generator is switched on. The plasma discharge of a power 250 Watts is maintained for a total period of 1 min (in order to clean and activate the lenses surfaces). Afterwards the 1,2-DACH vapor is introduced into the reactor chamber from DACH reservoir (maintained at 24° C.) at 0.15 mbar for 1 min. After this, the following parameters for the plasma polymerization of DACH are chosen: Argon flow rate for plasma excitation=5 sccm, Argon carrier gas flow rate for DACH transport=5 sccm, temperature of the DACH evaporation unit=24° C., the distance between the lower edge of the plasma zone and the substrates=5 cm, pressure=0.2 mbar, and plasma power=100 W. The lenses are treated for about 5 min with a pulsing glow discharge plasma (1 μsec. on, 3 μsec. off). After 5 min of deposition the plasma discharge is interrupted and DACH vapor is let to flow into reactor for additional 5 min. The reactor is then evacuated and maintained for 30 min at a pressure 0.008 mbar in order to remove residual monomer and activated spices. The internal pressure is brought to atmospheric by using dry nitrogen. The substrates are then turned over and the whole procedure is repeated to coat the other side of the substrates. The samples are then unloaded from the reactor and used for the subsequent photoinitiator linkage.

EXAMPLE A-2
Plasma Induced 2-Isocyanatoethyl Methacrylate Coating (Poly-IEM)

Lotrafilcon A contact lenses are, after extraction in isopropanol, placed on the Teflon holder within the plasma reactor equipped with external ring electrodes. The distance between the substrates and the lower edge of the plasma electrodes is 12 cm. The reactor is evacuated to a pressure of 0.010 mbar, and held at these conditions for 1 h. Then, the argon plasma gas flow rate into the plasma zone of the reactor is set to 20 sccm, the pressure in the reactor is adjusted to 0.07 mbar and the RF generator (27.12 MHz radio frequency generator, HFA Koppold & Co., Höhenkirchen, Germany) is switched on. The plasma discharge of a power 170 Watts is maintained for a total period of 1 min. Afterwards, the IEM vapor is introduced into the reactor chamber from IEM reservoir (maintained at 25° C.) at 0.15 mbar for 1 min. After this, the following parameters for the plasma induced polymerization of IEM are chosen: Argon flow rate for plasma excitation=20 sccm, argon carrier gas flow rate for monomer (IEM) transport=10 sccm, temperature of the monomer (IEM) evaporation unit=25° C., the distance between the lower edge of the plasma electrodes and the substrates=16 cm, pressure=0.10 mbar, and plasma power=60 W. After 5 min of deposition, the plasma discharge is interrupted; the reactor is evacuated and maintained for 30 min at a pressure 0.010 mbar. The internal pressure is then brought to atmospheric pressure by using dry nitrogen. The substrates are then turned over and the whole procedure is repeated to coat the other side of the substrates. The samples are then unloaded from the reactor and analyzed by ATR-FTIR measurements. Strong bands at about 2270 cm-1, which are characteristic for N=C=O groups, are clearly identified on all modified surfaces.

EXAMPLES A-3–A-6
Spray Coating on Contact Lenses Using Azido Aniline Hydrochloride A solution of 0.1 mg/mL azido aniline hydrochloride in methanol is given into a funnel of an airbrush (AERO-PRO 381™, Hansa). The solution is sprayed onto both sides of wet or dried Lotrafilcon A lenses (polysiloxane/perfluoroalkylpolyether copolymer) for the time as indicated in the Table below using a nitrogen pressure of 1.15 bar. Afterwards the lenses are irradiated 30 seconds using a UV lamp (LQ 400B, Gröbbel) with an intensity of 1.43 mW/cm$^2$ and a 305 nm cutoff filter. The whole process is optionally repeated. The lenses are then extracted in acetonitrile/methanol 80/20 overnight.

TABLE

| Example | Spray time in seconds/ Number of spray cycles | Lens surfaces before spraying |
|---------|-----------------------------------------------|-------------------------------|
| A-3     | 3/1                                           | dry                           |
| A-4     | 7/1                                           | dry                           |
| A-5     | 7/1                                           | wet                           |
| A-6     | 7/3                                           | dry                           |

EXAMPLE B-1
Surface Binding of the Reactive Photoinitiator Molecules

The amino functionalized contact lenses from Example A-1 are, immediately after plasma treatment with 1,2-DACH plasma, immersed into a 1% acetonitrile solution of the reactive photoinitiator prepared by the addition reaction from isophorone diiocyanate and 4-(2-hydroxyethoxy)phenyl 2-hydroxy-2-propyl ketone (Darocure 2959) (synthesis see EP 0 632 329). The amino groups on the lenses surfaces react with the isocyanato groups of the photoinitiator molecules for 12 h. After this time, the lenses are withdrawn from the reaction solution, washed and extracted in acetonitrile for 8 h and dried under reduced pressure for 2 h. The dried lenses are subsequently used for photografting.

EXAMPLE B-2
Surface Binding of Reactive Photoinitiator Molecules

The aminofunctionalized contact lenses from Example A-1 are, immediately after plasma treatment with 1,2-DACH plasma, immersed into a 1% acetonitrile solution of the reactive photoinitiator prepared by the addition reaction from isophorone diisocyanate and 2-ethyl-2-(dimethylamino)-1-[4-(2-hydroxyethoxy)phenyl]-4-penten-1-one (synthesis see WO 96/20796). The amino groups on the lenses surfaces react with the isocyanato groups of the photoinitiator molecules for 16 h. After this time, the lenses are withdrawn from the reaction solution, washed and extracted in acetonitrile for 12 h and dried under reduced pressure for 2 h. The dried lenses are subsequently used for photografting.

EXAMPLE B-3
Synthesis of a Reactive Photoinitiator Comprising a Reactive Amino Group A 1000 ml three-necked round botton flask is charged with a solution of 224.26 g (1 Mol) of Darocure 2959 in 400 ml of THF and 114.55 g (1 Mol) of methanesulfonyl chloride is added to the solution at RT. After cooling to 2° C., 101.2 g (1 Mol) of triethyl amine (TEA) and additional 200 ml of THF are added to the solution for 30 min under stirring. Slightly exothermal reaction is observed. The reaction mixture is than filtered through G3 glass frit filter and the TEA hydrochloride washed 2× with THF on the filter. The solvent from the filtrate is evaporated at 60° C. and the pressure 200 mbar using a Rotavapor. The yellow oil is than dissolved in 800 ml of $CH_2Cl_2$. The organic phase is washed 1× with 400 ml of deionized water, 2× with 400 ml of acidic water pH~1 and finally with 400 ml of deionized water. The organic phase is than dried over $MgSO_4$, filtered and concentrated to the constant weight by evaporating of the $CH_2Cl_2$ at a Rotavapor. 10.1 g of the dried compound is than dissolved in 30 ml $CH_2Cl_2$. After addition of 50 g of ethanolamine, the mixture is heated to 80° C. and stirred at this temperature for 1 h. The unreacted ethanolamine is than distilled off and the product is dissolved in 100 ml of 2 N HCl. After 20 minutes of stirring, the The isocyanato functionalized contact lenses from Example A-2 are, immediately after plasma treatment with 2-IEM plasma, immersed into 1% acetonitrile solution of the reactive photoinitiator prepared according to Example B-3. The isocyanate groups on the lenses surfaces react with the amino groups of the photoinitiator molecules for 12 hours. After this time, the lenses are withdrawn from the reaction solution, washed and extracted in acetonitrile for 8 hours and dried under reduced pressure for 2 hours. The dried lenses are subsequently used for photografting.

EXAMPLES B-5–B-8
Surface Binding of Reactive Photoinitiator Molecules

The aminofunctionalized contact lenses from Examples A-3–A-6 are immersed into a 1% by weight solution of the reactive photoinitiator prepared by the addition reaction from isophorone diisocyanate and 4-(2-hydroxyethoxy) phenyl 2-hydroxy-2-propyl ketone (Darocure 2959) (synthesis see EP 0 632 329) in acetonitrile. 3 drops of triethylamine (TEA) are then added to the solution. The amino groups on the lens surface react with the isocyanato groups of the photoinitiator molecules for 12 h. After this time, the lenses are withdrawn from the reaction solution, 3× washed and extracted in acetonitrile for 8 h and dried under reduced pressure for 2 h. The dried lenses are subsequently used for photografting.

EXAMPLE B-9–B-12
Surface Binding of the Reactive Photoinitiator Molecules

The aminofunctionalized contact lenses from Examples A-3 to A-6 are dried to the constant mass under reduced pressure. The lenses are then directly immersed into 1% by weight acetonitrile solution of the reactive photoinitiator prepared by the addition reaction from isophorone diisocyanate and 2-dimethylamino-2-benzyl-1-[4-(2-hydroxyethoxy)phenyl]-butan-1-one (synthesis see WO 96/20796 (5 ml solution/lens). 3 drops of triethylamine (TEA) are then added to the solution. The amino groups on the lens surface react with the isocyanato groups of the photoinitiator molecules for 12 h. After this time, the lenses are withdrawn from the reaction solution, 3× washed and extracted in acetonitrile for 6 h and dried under reduced pressure for 2 h. The dried lenses are subsequently used for photografting.

EXAMPLE C-1
Acrylamide Telomer ($M_n$ 1880)

A 2000 ml round bottom flask is charged with a solution of 142.1 g (2 Mol) acrylamide (Fluka 01696) in 700 ml of deionized water and cooled to −5° C. The frozen solution is evacuated to 50 mbar and after heating to RT filled with nitrogen gas. This freeze taw process is repeated three times.

1.1 g (4 mmol) of α,α'-azodiisobutyramidine dihydrochloride (Fluka 11633) and 17.5 g (0.154 Mol) cysteamine hydrochloride (Fluka 30080) are added to the cooled solution under nitrogen atmosphere. The clear and slightly yellowish solution is acidified with a few drops of 32% hydrochloric acid to pH 3.

With a constant stream of argon, this solution is cooled to 5° C. and slowly introduced onto an 'flow-through-reactor' consisting of an 2000 mL three-necked round-bottom flask, reflux condenser, thermometer, magnetic stirrer and a 30 cm Liebig-condenser, filled with glass wool. The Liebig condenser is heated to 70° C., the flask is heated to 60° C. The cooled solution is slowly dropped through the Liebig-condenser into the stirred flask using the Chromatography Pump Büchi 681. This takes 1 h 40 min. During this time the temperature in the flask is kept between 58–65° C. After the completed addition, the solution is stirred for 2 h at 60° C.

After cooling to RT, NaOH is added to the clear and slightly yellowish solution until pH 10.5 was reached. The product is purified through reverse osmosis, using Millipore cartridge with a cut-off at 1000 Da and freeze-dried. A bright-white solid product is obtained with a yield of 87%. The concentration of amino groups is determined via functional group titration (6.53 mEq/g), which corresponds to $M_n$ 1880 Da.

EXAMPLE C-2
Acrylamide Telomer ($M_n$ 1350)

A 1000 mL round bottom flask is charged with a solution of 99.5 g (1.46 mol) acrylamide (Fluka 01696), 1.27 g (4.68 mmol) α,α'-azodiisobutyramidine dihydrochloride (Fluka 11633) and 15.9 g (0.14 mol) cysteamine hydrochloride (Fluka 30080) in 300 ml of water. The clear and slightly yellowish solution is acidified with a few drops of 32% hydrochloric acid to pH 3. The stirred acidic solution is evacuated to 50 mbar and filled with argon. This is repeated three times.

With a constant stream of argon, this solution is poured into a 500 ml dropping funnel which was put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon.

The dropping funnel is put onto the Liebig condenser, which is heated to 65° C. The flask is heated to 60° C. The solution is slowly dropped through the Liebig condenser into the stirred flask. This takes 2 h. During this time the temperature in the flask is kept between 58–65° C. After the completed addition, the solution is stirred for 2 h at 60° C. NaOH is added to the clear and slightly yellowish solution until pH 10 is reached. The product is purified through reverse osmosis, using Millipore cartridge with a cut-off at 1000 Da and then freeze-dried for 18 h. A bright-white solid product is obtained in a yield of 77%. The concentration of amino groups is determined via functional group titration (0.70 mEq/g) which corresponds well with the sulfur-value of the elemental analysis (0.73 mEq/g). The corresponding number average molecular weight $M_n$ is 1350 Da.

EXAMPLE C-3
N,N-Dimethylacrylamide Telomer ($M_n$ 1850)

A 2000 ml round bottom flask is charged with a solution of 198.2 g (2 mol) acrylamide (Fluka 01696), 2.72 g (10 mmol) α,α'-azodiisobutyramidine dihydrochloride (Fluka 11633) and 24.8 g (0.22 mol) cysteamine hydrochloride (Fluka 30080) in 600 mL of water. The clear and slightly yellowish solution is acidified with a few drops of 32% hydrochloric acid to pH 3. The stirred acidic solution is evacuated to 50 mbar and filled with argon. This is repeated three times.

With a constant stream of Argon, this solution is poured into a 1000 mL dropping funnel which was put onto an 'flow-through-reactor' consisting of an 1000 mL three-necked round-bottom flask, reflux condenser, thermometer, magnetic stirrer and a 30 cm Liebig-condenser, which is filled with glass wool. The whole apparatus is constantly purged with Argon. The dropping funnel is put onto the Liebig condenser, which is heated to 60° C. The flask was also heated to 60° C. The solution is slowly dropped through the Liebig-condenser into the stirred flask. This takes 2.5 h. During this time the temperature in the flask is kept between 58–65° C. After the completed addition, the solution is stirred for 2 h at 60° C. 30% NaOH solution is added to the clear and slightly yellowish solution until pH 10 is reached. The product is purified through reverse osmosis, using a Millipore cartridge with a cut-off at 1000 Da and freeze-dried. A bright-white solid product is obtained in a yield of 75%. The concentration of amino groups is determined via functional group titration (0.54 mEq/g). The corresponding number average molecular weight $M_n$ is 1850 Da.

EXAMPLE D-1
Preparation of a Macromonomer Solution 3 g of acrylamide telomer with amino end group (amine titration=0.70 mEq/g), prepared by Example C-2 is dissolved in 30 mL of HPLC water. Argon is then let to bubble through the solution for the period of about 30 min. This mixture is then added to the equimolar amount (0.321 g) of isocyanatoethyl methacrylate (IEM, isocyanate titration=6.45 mEq/g) under stirring. The whole mixture was then stirred under argon flow for 12 h. After this reaction the mixture is used for subsequent reactions.

EXAMPLE D-2
Preparation of a Macromonomer Solution Comprising Sodium Hyaluronate 10 ml of the solution from Example D-1 and 10 ml of 0.5% aqueous solution of sodium hyaluronate (Denki Kagaku Kogyo, Mn.about.1.2×10$^{-6}$ Da) are mixed together and homogenized by stirring for 1 h. After adding of 0.2 g of NaCl to the solution and 10 min stirring, the mixture is filtered through 1.2 μm Teflon filter, degassed by repeated (3×) evacuation and bubbling with argon in order to remove dissolved oxygen and used for photografting.

EXAMPLE D-3
Preparation of s Macromonomer Solution Comprising Poly-N-Vinylpyrrolidone 10 ml of the solution from Example D-1 and 10 ml of 1% aqueous solution of poly-N-vinylpyrrolidone (Polysciences, Inc. Cat #01052, Mw 40000, pharmaceutical grade) are mixed together and homogenized by stirring for 1 h. After adding of 0.2 g of NaCl to the solution and 10 minutes stirring, the mixture is filtered through a 0.45 μm Teflon filter, degassed by repeated (3×) evacuation and bubbling with argon in order to remove dissolved oxygen and used for photografting.

EXAMPLE D-4
Preparation of a Macromonomer Solution Comprising Carbopol 981 NF 10 ml of the solution from Example D-1 and 10 ml of 0.5% aqueous solution of Carbopol 981 NF (BFGoodrich) are mixed together and homogenized by stirring for 1 h. After adding of 0.2 g of NaCl to the solution and 10 min stirring, the mixture is filtered through a 1.2 μm Teflon filter, degassed by repeated (3×) evacuation and bubbling with argon in order to remove dissolved oxygen and used for photografting.

EXAMPLE D-5
Preparation of a Macromonomer Solution Comprising Sodium Hyaluronate 10 ml of the solution from Example D-1 and 10 ml of 0.2% aqueous solution of sodium hyaluronate were mixed together and homogenized by stirring for 1 h. After adding of 0.2 g of NaCl to the solution and 10 min stirring, the mixture is filtered through a 1.2 μm Teflon filter, degassed by repeated (3×) evacuation and bubbling with argon in order to remove dissolved oxygen and used for photografting.

EXAMPLE D-6
Preparation of a Macromonomer Solution Comprising Sodium Hyaluronate 3 g of N,N-dimethylacrylamide telomer with amino end group (amine titration=0.53 mEq/g), prepared by Example C-3 are dissolved in 15 ml of HPLC water. This mixture is then added to the equimolar amount (0.25 g) of isocyanatoethyl methacrylate (IEM, isocyanate titration=6.45 mEq/g) under stirring. The whole mixture is then stirred under argon flow for 12 h. After adding of 15 mL of the 0.2% aqueous solution of sodium hyaluronate to the solution and 40 min stirring, the mixture is filtered through a 1.2 μm Teflon filter, degassed with nitrogen in order to remove oxygen and used for photografting.

EXAMPLE E-1
Photografting of a Macromonomer Solution Comprising Sodium Hyaluronate Onto a Contact Lens Surface In a glove box, 1 mL of the solution from Example D-2 is introduced into a small Petri dish of a volume of about 2 mL. The lens from Example B-1, carrying covalently linked photoinitiator molecules on its surface, is then placed into this solution and an additional 0.5 mL of the degassed solution is added on the lens in order to cover the whole lens with the solution. After 10 min, the Petri dish with the lens under the solution is exposed to 14 mW ultraviolet light for a period of about 2 min. The lens is then turned over and the exposition is repeated by applying 14 mW UV light for an additional 2 min.

The modified lens is then withdrawn from the solution, washed 3× in distilled water, continuously extracted in ultra pure water for 16 h and analyzed by contact angle measurements.

Water/air contact angles on the modified lens are 0° adv., 0° rec., 0° hysteresis. In comparison, the contact angles of non-modified lens are 101° adv., 64° rec., 37° hysteresis. The lens holds continuous water layer on the surface for over 1 min.

EXAMPLE E-2
Photografting of a Macromonomer Solution Comprising Carbopol 981 NF onto a Contact Lens Surface 1 ml of the solution from Example D-4 is introduced into a small Petri dish of a volume of about 2 ml in a glove box. The dried lens from Example B-1, carrying covalently linked photoinitiator molecules on its surface, is then placed into this solution and an additional 1 mL of the degassed solution was added on the lens in order to cover the whole lens with the solution. After 15 min, the Petri dish with the lens in the solution is exposed to 14 mW ultraviolet light for a period of about 2 min. The lens is then turned over and the exposition was repeated by applying 14 mW UV light for an additional 2 min.

The modified lens is then withdrawn from the solution, washed twice in distilled water, continuously extracted in ultra pure water for 16 h and analyzed by AFM, ATR-FTIR and contact angle measurements.

The thickness of the coating is in the range of 300–400 nm as determined by AFM. Water/air contact angles on the modified lens are 4° adv., 0° rec., 4° hysteresis. In comparison, the contact angles of non-modified lens are 101° adv., 64° rec., 37° hysteresis. The lens holds continuous water layer on the surface for over 1 min.

EXAMPLE E-3
Photografting of a Macromonomer Solution Comprising Poly-N-vinlpyrrolidone Onto a Contact Lens Surface Two lenses from Example B-1 are coated in accordance with Example E-1, but instead of the solution from Example D-2, the solution from Example D-3 is used for UV coupling. Water/air contact angles on the modified lenses are 5° adv., 0° rec., 5° hysteresis.

EXAMPLE E-4
Photografting of a Macromonomer Solution Comprising Sodium Hyaluronate Onto a Contact Lens Surface 1 ml of the solution from Example D-5 is introduced into a small Petri dish of a volume of about 2 ml in a glove box. The dried lens from Example B-1, carrying covalently linked photoinitiator molecules on its surface, is then placed into this solution and an additional 1 mL of the degassed solution is added on the lens in order to cover the whole lens with the solution. After 15 min the Petri dish with the lens in the solution is exposed to 15 mW ultraviolet light for a period of about 1 min. The modified lens is then withdrawn from the solution, washed twice in distilled water, continuously extracted in ultra pure water for 16 h and analyzed by ATR-FTIR and contact angle measurements.

The thickness of the coating is in the range of 200–300 nm as determined by AFM. Water/air contact angles on the modified lens are 0° adv., 0° rec., 0° hysteresis. In comparison, the contact angles of non-modified lens are 101° adv., 64° rec., 37° hysteresis. The lens holds continuous water layer on the surface for over 1 min.

EXAMPLE E-5
Photografting of a Macromonomer Solution Comprising Sodium Hyaluronate Onto a Contact Lens Surface Five lenses from Example B-4 are coated in accordance with Example E-1, but instead of the solution from Example D-2, the solution from Example D-5 is used for UV coupling. Water/air contact angles on the modified lenses are 4° adv., 0° rec., 4° hysteresis.

EXAMPLE E-6
Photografting of a Macromonomer Solution Comprising Sodium Hyaluronate Onto a Contact Lens Surface Five lenses from Example B-4 are coated in accordance with Example E-5, but instead of the solution from Example D-5, the solution from Example D-2 is used for UV coupling. Water/air contact angles on the modified lenses are 0° adv., 0° rec., 0° hysteresis.

EXAMPLE E-7
Photografting of a Macromonomer Solution Comprising Sodium Hyaluronate Onto a Contact Lens Surface Five lenses from Example B-4 are coated in accordance with Example E-5, but instead of the solution from Example D-5, the solution from Example D-6 is used for UV coupling. Water/air contact angles on the modified lenses are 15° adv., 9° rec., 6° hysteresis.

What is claimed is:

1. A process for coating a biomedical device, which comprises:
   (a) covalently attaching initiator moieties to the surface of an inorganic or organic bulk material;
   (b) initiating, thermally or by UV radiation, graft-polymerization of a hydrophilic ethylenically unsaturated macromonomer on the surface of the bulk material in the presence of a biocompatible hydrophilic polymer being devoid of polymerizable ethylenically unsaturated groups to form a hydrophilic coating,
   wherein the hydrophilic coating comprises a graft polymer formed by the polymerization of the hydrophilic macromonomer and the biocompatible hydrophilic polymer, wherein polymer chains of the graft polymer are covalently bound to the surface of the bulk material,
   wherein the biocompatible hydrophilic polymer is not covalently bound neither to the surface of the bulk material nor to the polymer chains of the graft polymer, but is entangled with the polymer chains of the graft polymer, and
   wherein the biocompatible hydrophilic polymer is capable of being released from the coating under physiological conditions.

2. A process according to claim 1, wherein the attachment of the initiator moieties to the bulk material comprises:
   (a) providing a bulk material surface with H-active groups;
   (b) reacting the bulk material surface with a functional polymerization initiator having a functional group that is co-reactive to said H-active groups.

3. A process according to claim 1, wherein the attachment of the initiator moieties to the bulk comprises:
   (a) reacting the surface of the bulk material surface with a compound of formula

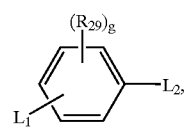

(1)

wherein $R_{29}$ is $C_1$–$C_4$-alkyl, $C_1$–$C_4$-alkoxy, hydroxy, sulfo, nitro, trifluoromethyl or halogen, g is an integer from 0 to 2, $L_1$ is a group, which functions as a triggerable precursor for carbene or nitrene formation, $L_2$ is amino, $C_1$–$C_4$-alkylamino, hydroxy, glycidyl, carboxy, a carboxy derivative, isocyanato or isothiocyanato, or is a radical of formula

(1a), $L_2'$ is amino, $C_1$–$C_4$-alkylamino, hydroxy, carboxy, a carboxy derivative, isocyanato, isothiocyanato, —O-glycidyl or —O—C(O)—(CH$_2$)$_{n1}$—X$_2$, wherein h1 is from 1 to 4 and X$_2$ is carboxy or a derivative thereof, $L_3$ is —NH—, —NC$_1$–C$_6$alkyl-, —O—, —C(O)O—, —C(O)NH—, —NHC(O)NH—, —NHC(O)O— or —OC(O)NH—;

(spacer) is linear or branched $C_1$–$C_{200}$-alkylene which may be substituted by hydroxyl, -(alk')-O—

$(CH_2CH_2O)_{18-160}$-(alk') $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene, or $C_1$–$C_6$-alkylene-$C_3$–$C_8$-cycloalkylene-$C_1$–$C_6$-alkylene, wherein alk' is $C_1$–$C_6$-alkylene; and h is the number 0 or 1;

(b) reacting the so modified surface with a functional polymerization initiator having a functional group that is co-reactive to $L_2$ or $L_2'$.

4. A process according to claim 3, wherein step (a) comprises applying the compound of formula (1) to the surface of the bulk material and fixing said compound of formula (1) onto the surface of the bulk material using radiation.

5. A process according to claim 3, wherein $L_1$ is the radical of formula

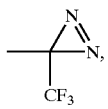

g is 0, and $L_2$ is carboxy or a derivative thereof or is a radical of formula $L_3$-(spacer)-$L_2'$, wherein $L_3$ is —C(O)O— or —C(O)NH—, (spacer) is linear $C_2$–$C_{12}$-alkylene or —($C_2$–$C_3$-alkylene)-O—$(CH_2CH_2O)_{18-92}$—($C_2$–$C_3$-alkylene)-, and $L_2'$ is carboxy, a carboxy derivative or a radical —O—C(O)—$(CH_2)_2$—$X_2$, wherein $X_2$ is carboxy or a carboxy derivative.

6. A process according to claim 3, wherein $L_1$ is the azide radical —$N_3$, g is 0 or 1, $R_{29}$ is methyl, methoxy, hydroxy or nitro, and $L_2$ is amino, carboxy, a carboxy derivative, isocyanato, isothiocyanato or a radical of formula —$L_3$-(spacer)-$L_2'$, wherein $L_3$ is —NH—C(O)O— or —C(O)NH—, (spacer) is linear $C_2$–$C_{12}$-alkylene or —($C_2$–$C_3$-alkylene)-O—$(CH_2CH_2O)_{18-92}$—($C_2$–$C_3$-alkylene)-, and $L_2'$ is carboxy, a carboxy derivative or a radical —O—C(O)—$(CH_2)_2X_2$, wherein $X_2$ is carboxy or a carboxy derivative.

7. A process according to claim 2, wherein the functional polymerization initiator is a photoinitiator of formula (3a)

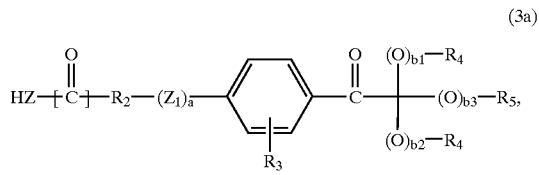

(3b)

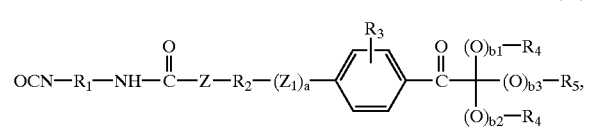

or (3c)

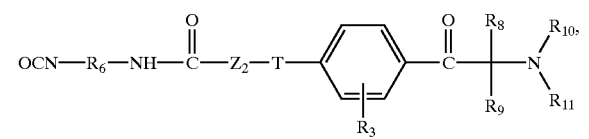

wherein Z is bivalent —O—, —NH— or —$NR_{12}$—; $Z_1$ is —O—, —O—(O)C—, —C(O)—O— or —O—C(O)—O—; $R_3$ is H, $C_1$–$C_{12}$-alkyl, $C_1$–$C_{12}$-alkoxy or N—$C_1$–$C_{12}$-alkylamino; $R_4$ and $R_5$ are each independently of the other H, linear or branched $C_1$–$C_8$-alkyl, $C_1$–$C_8$-hydroxyalkyl or $C_6$–$C_{10}$-aryl, or the groups $R_4$—$(O)_{b1}$ and $R_4$—$(O)_{b2}$— together are —$(CH_2)_c$— wherein c is an integer from 3 to 5, or the groups $R_4$—$(O)_{b1}$—$R_4$—$(O)_{b2}$— and $R_5$—$(O_1)_{b3}$— together are a radical of the formula

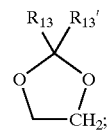

$R_2$ is a direct bond or linear or branched $C_1$–$C_8$-alkylene that is unsubstituted or substituted by —OH and/or is uninterrupted or interrupted by one or more groups —O—, —O—C(O)— or —O—C(O)—O—; $R_1$ is branched $C_3$–$C_{18}$-alkylene, unsubstituted or $C_1$–$C_4$-alkyl- or $C_1$–$C_4$-alkoxy-substituted $C_8$–$C_{10}$-arylene, or unsubstituted or $C_1$–$C_4$-alkyl- or $C_1$–$C_4$-alkoxy-substituted $C_7$–$C_{18}$-aralkylene, unsubstituted or $C_1$–$C_4$-alkyl- or $C_1$–$C_4$-alkoxy-substituted $C_3$–$C_8$-cycloalkylene, unsubstituted or $C_1$–$C_4$-alkyl- or $C_1$–$C_4$-alkoxy-substituted $C_3$–$C_8$-cycloalkylene-$C_yH_{2y}$— or unsubstituted or $C_1$–$C_4$-alkyl- or $C_1$–$C_4$-alkoxy-substituted —$C_yH_{2y}$—($C_3$–$C_8$-cycloalkylene)-$C_yH_{2y}$— wherein y is an integer from 1 to 6; $R_8$ independently has the same definitions as $R_1$ or is linear $C_3$–$C_{18}$-alkylene; $R_{12}$ is linear or branched $C_1$–$C_8$-alkyl; T is bivalent —O—, —NH—, —S—, $C_1$–$C_8$-alkylene or

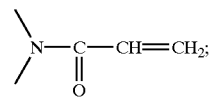

$Z_2$ is a direct bond or —O—$(CH_2)_d$— or —$(OCH_2CH_2)_d$— wherein d is an integer from 1 to 6 and the terminal $CH_2$ group of which is each linked to the adjacent T in formula (3c); $R_8$ is linear or branched $C_1$–$C_8$-alkyl, $C_2$–$C_8$-alkenyl or $C_8$–$C_{10}$-aryl-$C_1$–$C_8$-alkyl; $R_9$ independently of $R_8$ has the same definitions as $R_8$ or is $C_6$–$C_{10}$-aryl, or $R_8$ and $R_9$ together are —$(CH_2)_e$— wherein e is an integer from 2 to 6; $R_{10}$ and $R_{11}$ are each independently of the other linear or branched $C_1$–$C_8$-alkyl that may be substituted by $C_1$–$C_4$-alkoxy, or $C_8$–$C_{10}$-aryl-$C_1$–$C_8$-alkyl or $C_2$–$C_8$-alkenyl; or $R_{10}$ and $R_{11}$ together are —$(CH_2)_{f1}$—$Z_3$—$(CH_2)_{f2}$— wherein $Z_3$ is a direct bond, —O—, —S— or —$NR_7$—, and $R_7$ is H or $C_1$–$C_8$-alkyl and f1 and f2 are each independently of the other an integer from 2 to 4; $R_{13}$ and $R_{13}'$ are each independently of the other H, $C_1$–$C_8$-alkyl, $C_3$–$C_8$-cycloalkyl, benzyl or phenyl; and a, a1, b1, b2 and b3 are each independently of the other 0 or 1; subject to the provisos that b1 and b2 are each 0 when $R_{15}$ is H; that the total of (b1+b2+b3) is not exceeding 2; and that a is 0 when $R_{12}$ is a direct bond.

8. A process according to claim 1, wherein a macromonomer of formula (4)

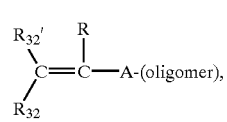

is applied in step (b), wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

—C(O)—$(A_1)_n$—X—  (5a) or

—$(A_2)_m$—NH—C(O)—X—  (5b); or

—$(A_2)_m$—X—C(O)—  (5c); or

—C(O)—NH—C(O)—X—  (5d); or

—C(O)—$X_1$—(alk*)—X—C(O)—  (5e); or

A and $R_{32}$, together with the adjacent double bond, are a radical of formula

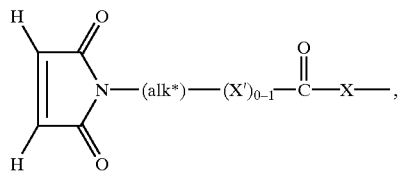
(5f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH—(Alk*)—C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_8$–$C_{10}$-arylene, $C_7$–$C_{18}$-aralkylene, $C_8$–$C_{10}$-arylene-$C_1$–$C_2$-alkylene-$C_8$–$C_{10}$-arylene, $C_3$–$C_8$-cycloalkylene, $C_3$–$C_8$-cycloalkylene-$C_1$–$C_8$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene:

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

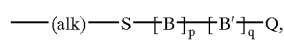
(6a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

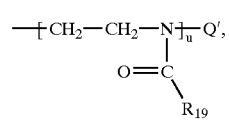
(6b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

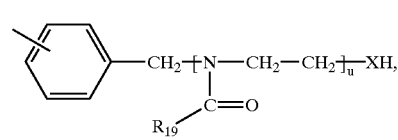
(6b')

wherein $R_{19}$, X and u are as defined above, or (iv) the radical of an oligomer of formula

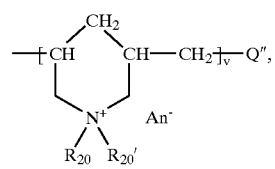
(6c)

wherein $R_{20}$ and $R_{20}'$ are each independently $C_1$–$C_4$-alkyl, $An^-$ is an anion, v is an integer from 2 to 250, and Q" is a monovalent group that is suitable to act as a polymerization chain-reaction terminator; or (v) the radical of an oligopeptide of formula —$(CHR_{21}$—C(O)—NH$)_t$—$CHR_{21}$—COOH  (6d) or —$CHR_{21}$—(NH—C(O)—$CHR_{21})_t$—$NH_2$  (6d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or (vi) the radical of a polyalkylene oxide of formula -(alk*-O)$_z$—[$CH_2$—$CH_2$—O]$_r$—[$CH_2$—CH($CH_3$)—O]$_s$—$R_{34}$ (6e), wherein $R_{34}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (5a), (5b) or (5d) or A and $R_{32}$, together with the adjacent double bond, are a radical of formula (5f) if (oligomer) is a radical of formula (6b), (6c), (6d) or (6e) or is the radical of an oligosaccharide;

A is a direct bond if (oligomer) is a radical of formula (6b'); and

A is a radical of formula (5c) or (5e) if (oligomer) is a radical of formula (6d').

9. A process according to claim 8, wherein R is hydrogen or methyl, wherein $R_{32}$ and $R_{32}'$ are each hydrogen, and wherein A is a radical of the formula (5a) and (oligomer) is a radical of formula (6a).

10. A process according to claim 8, wherein (oligomer) is a radical of formula

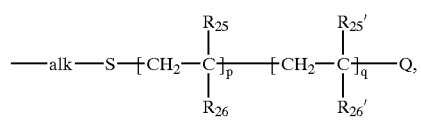
(6a')

wherein (alk) is $C_2$–$C_4$-alkylene, $R_{25}$ and $R_{25}'$ are each independently hydrogen or methyl, Q is a monovalent group that is suitable to act as a polymerization chain-reaction terminator, p and q are each independently an integer from 0 to 100 wherein the total of (p+q) is an integer from 5 to 100, and $R_{26}$ and $R_{26}'$ are each independently a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose; a radical —CO—$NY_1Y_2$, wherein $Y_1$ and $Y_2$ are each independently of the other hydrogen or $C_1$–$C_2$-alkyl which is unsubstituted or substituted by hydroxy, or $Y_1$ and $Y_2$ together with the adjacent N-atom form a N—$C_1$–$C_2$-alkylpiperazino or morpholino ring; a heterocyclic radical selected from the group consisting of N-pyrrolidonyl, 2- or 4-pyridinyl, 2-methylpyridinoder 4-hydroxypyridinyl, N-ε-caprolactamyl, N-imidazolyl, 2-methylimidazol-1-yl, N-morpholinyl and 4-N-methylpiperazin-1-yl; —COOH; —$SO_3H$; o-, m- or p-sulfophenyl; o-, m- or p-sulfomethylphenyl; a radical —$CONY_5Y_6$ wherein $Y_5$ is $C_2$–$C_4$-alkyl substituted by sulfo, and $Y_8$ is hydrogen; $C_1$–$C_4$-alkyl which is substituted by —$NR_{23}R_{23}'R_{23}''^+$ $An^-$ wherein $R_{23}$, $R_{23}'$ and $R_{23}''$ are each independently of another hydrogen or $C_1$–$C_4$-alkyl and $An^-$ is an anion; a radical —$C(O)OY_7$ wherein $Y_7$ is $C_2$–$C_4$-alkyl, which is substituted by —$NR_{23}R_{23}'R_{23}''^+An^-$ and is further unsubstituted or substituted by hydroxy, wherein $R_{23}$, $R_{23}'$, $R_{23}''$ and $^+An^-$ are as defined; and a radical —C(O)O—$CH_2$—CH($OY_8$)—$CH_2$—O—$PO_2$—$(CH_2)_2$—$N(CH_3)_3^+$, wherein $Y_8$ is hydrogen or the acyl radical of a higher fatty acid.

11. A process according to claim 8, wherein in step (b) a macromonomer of formula

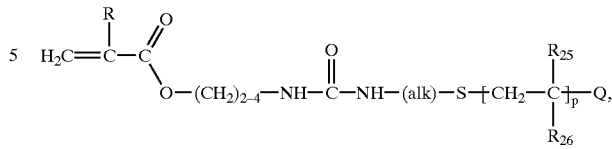
(4b)

is applied, wherein R is hydrogen or methyl, (alk) is $C_2$–$C_4$-alkylene, $R_{25}$ is hydrogen or methyl, p is an integer of 5 to 50, Q is a monovalent group that is suitable to act as a polymerization chain-reaction terminator, and $R_{26}$ is a radical —$CONH_2$, —$CON(CH_3)_2$ or

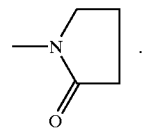
.

12. A process according to claim 1, wherein the biocompatible hydrophilic polymer applied in step (b) is selected from the group consisting of hyaluronic acid, sodium hyaluronate, chondroitin sulfate, heparin, dextran and mucin.

13. A process according to claim 1, wherein the biocompatible hydrophilic polymer applied in step (b) is selected from the group consisting of carboxymethylcellulose, carboxyalkylchitin and carboxyalkylchitosan.

14. A process according to claim 1, wherein the biocompatible hydrophilic polymer applied in step (b) is selected from the group consisting of a polyoxyalkylene amine, polyethylene glycol, poly-HEMA, a crosslinked polyacrylic acid based polymer, polyacrylamide, polyvinylpyrrolidone and polyvinylalcohol.

15. A process according to claim 1, wherein in step (b) bioactive material or polymer is added.

16. A process according to claim 2, wherein the biomedical device is a contact lens, an intraocular lens or an artificial cornea.

17. A process according to claim 4, wherein the radiation is UV.

* * * * *